US010772670B2

United States Patent
Hoey et al.

(10) Patent No.: US 10,772,670 B2
(45) Date of Patent: *Sep. 15, 2020

(54) SYSTEMS AND METHODS FOR TREATING PROSTATE CANCER

(71) Applicant: Boston Scientific Scimed, Inc., Maple Grove, MN (US)

(72) Inventors: Michael Hoey, Shoreview, MN (US); Grant Mauch, Delano, MN (US); Mark Schrom, Forest Lake, MN (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1191 days.

This patent is subject to a terminal disclaimer.

(21) Appl. No.: 14/773,853

(22) PCT Filed: Mar. 14, 2014

(86) PCT No.: PCT/US2014/028985
§ 371 (c)(1),
(2) Date: Sep. 9, 2015

(87) PCT Pub. No.: WO2014/153082
PCT Pub. Date: Sep. 25, 2014

(65) Prior Publication Data
US 2016/0015445 A1 Jan. 21, 2016

Related U.S. Application Data

(60) Provisional application No. 61/785,649, filed on Mar. 14, 2013.

(51) Int. Cl.
*A61B 8/08* (2006.01)
*A61B 18/04* (2006.01)
(Continued)

(52) U.S. Cl.
CPC .......... *A61B 18/042* (2013.01); *A61B 8/0841* (2013.01); *A61B 18/04* (2013.01);
(Continued)

(58) Field of Classification Search
CPC .......... A61B 2017/00274; A61B 2018/00547; A61B 18/042; A61B 8/0841; A61B 8/04;
(Continued)

(56) References Cited

U.S. PATENT DOCUMENTS

| 408,899 A | 8/1889 | Small |
| 1,719,750 A | 7/1929 | Bridge et al. |

(Continued)

FOREIGN PATENT DOCUMENTS

| CN | 2061443 U | 9/1990 |
| CN | 2418844 Y | 2/2001 |

(Continued)

OTHER PUBLICATIONS

US 5,326,343 A, 07/1994, Rudie et al. (withdrawn)
(Continued)

*Primary Examiner* — Linda C Dvorak
*Assistant Examiner* — Annabeth E Rodriguez
(74) *Attorney, Agent, or Firm* — Bookoff McAndrews, PLLC

(57) ABSTRACT

A vapor delivery needle and method is provided that is adapted for treating prostate cancer. The energy delivery probe can apply condensable vapor energy to tissue, such as a peripheral zone tissue in a human prostate. In one method, a needle is introduced into peripheral zone tissue of a human prostate, and vapor media is delivered through the needle to ablate peripheral zone tissue without ablating non-peripheral zone tissue. Systems for treating prostate cancer with vapor therapy are also provided.

9 Claims, 14 Drawing Sheets

(51) Int. Cl.
*A61B 18/00* (2006.01)
*A61B 90/00* (2016.01)

(52) U.S. Cl.
CPC ............. *A61B 2018/00005* (2013.01); *A61B 2018/00011* (2013.01); *A61B 2018/00017* (2013.01); *A61B 2018/00023* (2013.01); *A61B 2018/00101* (2013.01); *A61B 2018/00547* (2013.01); *A61B 2018/00577* (2013.01); *A61B 2018/00642* (2013.01); *A61B 2018/00702* (2013.01); *A61B 2018/00744* (2013.01); *A61B 2018/00791* (2013.01); *A61B 2018/00821* (2013.01); *A61B 2018/044* (2013.01); *A61B 2018/048* (2013.01); *A61B 2090/378* (2016.02); *A61B 2090/3784* (2016.02); *A61B 2218/007* (2013.01)

(58) Field of Classification Search
CPC ...... A61B 2090/378; A61B 2090/3784; A61B 2018/00577; A61B 2018/00642; A61B 2018/00702; A61B 2018/00744; A61B 2018/00821; A61B 2018/044; A61B 2018/048; A61B 2218/007
See application file for complete search history.

(56) References Cited

U.S. PATENT DOCUMENTS

| | | |
|---|---|---|
| 4,672,963 A | 6/1987 | Barken |
| 4,920,982 A | 5/1990 | Goldstein |
| 4,950,267 A | 8/1990 | Ishihara et al. |
| 5,117,482 A | 5/1992 | Hauber |
| 5,222,185 A | 6/1993 | McCord, Jr. |
| 5,249,585 A | 10/1993 | Turner et al. |
| 5,300,099 A | 4/1994 | Rudie |
| 5,312,399 A | 5/1994 | Hakky et al. |
| 5,330,518 A | 7/1994 | Neilson et al. |
| 5,366,490 A * | 11/1994 | Edwards .............. A61B 18/00 607/99 |
| 5,370,609 A | 12/1994 | Drasler et al. |
| 5,370,675 A | 12/1994 | Edwards et al. |
| 5,370,677 A | 12/1994 | Rudie et al. |
| 5,385,544 A | 1/1995 | Edwards et al. |
| 5,409,453 A | 4/1995 | Lundquist et al. |
| 5,413,588 A | 5/1995 | Rudie et al. |
| 5,421,819 A | 6/1995 | Edwards et al. |
| 5,435,805 A | 7/1995 | Edwards et al. |
| 5,464,437 A | 11/1995 | Reid et al. |
| 5,470,308 A | 11/1995 | Edwards et al. |
| 5,470,309 A | 11/1995 | Edwards et al. |
| 5,484,400 A | 1/1996 | Edwards et al. |
| 5,499,998 A | 3/1996 | Meade |
| 5,531,676 A | 7/1996 | Edwards et al. |
| 5,531,763 A | 7/1996 | Mastri et al. |
| 5,542,915 A | 8/1996 | Edwards et al. |
| 5,542,916 A | 8/1996 | Hirsch et al. |
| 5,545,171 A | 8/1996 | Sharkey et al. |
| 5,549,644 A | 8/1996 | Lundquist et al. |
| 5,554,110 A | 9/1996 | Edwards et al. |
| 5,556,377 A | 9/1996 | Rosen et al. |
| 5,558,673 A | 9/1996 | Edwards et al. |
| 5,588,960 A | 12/1996 | Edwards et al. |
| 5,591,125 A | 1/1997 | Edwards et al. |
| 5,599,294 A | 2/1997 | Edwards et al. |
| 5,601,591 A | 2/1997 | Edwards et al. |
| 5,628,770 A | 5/1997 | Thome et al. |
| 5,630,794 A | 5/1997 | Lax et al. |
| 5,645,528 A | 7/1997 | Thome |
| 5,667,488 A | 9/1997 | Lundquist et al. |
| 5,672,153 A | 9/1997 | Lax et al. |
| 5,709,680 A | 1/1998 | Yates et al. |
| 5,720,718 A | 2/1998 | Rosen et al. |
| 5,720,719 A | 2/1998 | Edwards et al. |
| 5,776,176 A | 7/1998 | Rudie |
| 5,792,070 A | 8/1998 | Kauphusman et al. |
| 5,797,903 A | 8/1998 | Swanson et al. |
| 5,800,486 A | 9/1998 | Thome et al. |
| 5,807,395 A | 9/1998 | Mulier et al. |
| 5,830,179 A | 11/1998 | Mikus et al. |
| 5,843,144 A | 12/1998 | Rudie et al. |
| 5,849,011 A | 12/1998 | Jones et al. |
| 5,861,002 A * | 1/1999 | Desai .................. A61B 8/0841 606/139 |
| 5,861,021 A | 1/1999 | Thome et al. |
| 5,871,481 A | 2/1999 | Kannenberg et al. |
| 5,873,877 A | 2/1999 | McGaffigan et al. |
| 5,897,553 A | 4/1999 | Mulier et al. |
| 5,899,932 A | 5/1999 | Dann et al. |
| 5,938,692 A | 8/1999 | Rudie |
| 5,944,715 A | 8/1999 | Goble et al. |
| 5,951,515 A | 9/1999 | Osterlind |
| 5,957,922 A | 9/1999 | Imran |
| 5,961,458 A * | 10/1999 | Carroll .................. A61B 6/032 250/336.1 |
| 5,964,752 A | 10/1999 | Stone |
| 5,964,756 A | 10/1999 | McGaffigan et al. |
| 5,976,123 A | 11/1999 | Baumgardner et al. |
| 5,987,360 A | 11/1999 | McGrath et al. |
| 5,990,465 A | 11/1999 | Nakaoka et al. |
| 6,007,571 A | 12/1999 | Neilson et al. |
| 6,009,351 A | 12/1999 | Flachman |
| 6,017,358 A | 1/2000 | Yoon et al. |
| 6,017,361 A | 1/2000 | Mikus et al. |
| 6,036,631 A | 3/2000 | McGrath et al. |
| 6,036,713 A | 3/2000 | Kieturakis |
| 6,053,909 A | 4/2000 | Shadduck |
| 6,063,081 A | 5/2000 | Mulier et al. |
| 6,067,475 A | 5/2000 | Graves et al. |
| 6,077,257 A | 6/2000 | Edwards et al. |
| 6,113,593 A | 9/2000 | Tu et al. |
| 6,122,551 A | 9/2000 | Rudie et al. |
| 6,123,083 A | 9/2000 | McGrath et al. |
| 6,147,336 A | 11/2000 | Oshijima et al. |
| 6,148,236 A | 11/2000 | Dann |
| 6,156,036 A | 12/2000 | Sussman et al. |
| 6,161,049 A | 12/2000 | Rudie et al. |
| 6,179,805 B1 | 1/2001 | Sussman et al. |
| 6,179,836 B1 | 1/2001 | Eggers et al. |
| 6,206,847 B1 | 3/2001 | Edwards et al. |
| 6,210,404 B1 | 4/2001 | Shadduck |
| 6,223,085 B1 | 4/2001 | Dann et al. |
| 6,231,591 B1 | 5/2001 | Desai |
| 6,238,389 B1 | 5/2001 | Paddock et al. |
| 6,238,391 B1 | 5/2001 | Olsen et al. |
| 6,238,393 B1 | 5/2001 | Mulier et al. |
| 6,241,702 B1 | 6/2001 | Lundquist et al. |
| 6,258,087 B1 | 7/2001 | Edwards et al. |
| 6,272,384 B1 | 8/2001 | Simon et al. |
| 6,287,297 B1 | 9/2001 | Woodruff et al. |
| 6,302,903 B1 | 10/2001 | Mulier et al. |
| 6,312,391 B1 | 11/2001 | Ramadhyani et al. |
| 6,315,777 B1 | 11/2001 | Comben |
| 6,348,039 B1 | 2/2002 | Flachman et al. |
| 6,398,759 B1 | 6/2002 | Sussman et al. |
| 6,409,722 B1 | 6/2002 | Hoey et al. |
| 6,423,027 B1 | 7/2002 | Gonon |
| 6,440,127 B2 | 8/2002 | McGovern et al. |
| 6,461,296 B1 | 10/2002 | Desai |
| 6,494,902 B2 | 12/2002 | Hoey et al. |
| 6,496,737 B2 | 12/2002 | Rudie et al. |
| 6,508,816 B2 | 1/2003 | Shadduck |
| 6,517,534 B1 | 2/2003 | McGovern et al. |
| 6,524,270 B1 | 2/2003 | Bolmsjo et al. |
| 6,537,248 B2 | 3/2003 | Mulier et al. |
| 6,537,272 B2 | 3/2003 | Christopherson et al. |
| 6,544,211 B1 | 4/2003 | Andrew et al. |
| 6,551,300 B1 | 4/2003 | McGaffigan |
| 6,565,561 B1 | 5/2003 | Goble et al. |
| 6,575,929 B2 | 6/2003 | Sussman et al. |
| 6,575,968 B1 | 6/2003 | Eggers et al. |
| 6,579,270 B2 | 6/2003 | Sussman et al. |
| 6,589,201 B1 | 7/2003 | Sussman et al. |
| 6,607,529 B1 | 8/2003 | Jones et al. |

(56) References Cited

U.S. PATENT DOCUMENTS

| | | | |
|---|---|---|---|
| 6,638,275 B1 | 10/2003 | McGaffigan et al. |
| 6,640,139 B1 | 10/2003 | Ueberle |
| 6,669,694 B2 | 12/2003 | Shadduck |
| 6,676,628 B2 | 1/2004 | Sussman et al. |
| 6,706,039 B2 | 3/2004 | Mulier et al. |
| 6,716,252 B2 | 4/2004 | Lazarovitz et al. |
| 6,719,738 B2 | 4/2004 | Mehier |
| 6,726,696 B1 | 4/2004 | Houser et al. |
| 6,730,079 B2 | 5/2004 | Lovewell |
| 6,736,810 B2 | 5/2004 | Hoey et al. |
| 6,740,108 B1 | 5/2004 | Just et al. |
| 6,760,616 B2 | 7/2004 | Hoey et al. |
| 6,780,178 B2 | 8/2004 | Palanker et al. |
| 6,827,718 B2 | 12/2004 | Hutchins et al. |
| 6,855,141 B2 | 2/2005 | Lovewell |
| 6,887,237 B2 | 5/2005 | McGaffigan |
| 6,905,475 B2 | 6/2005 | Hauschild et al. |
| 6,911,028 B2 | 6/2005 | Shadduck |
| 6,969,376 B2 | 11/2005 | Takagi et al. |
| 6,974,455 B2 | 12/2005 | Garabedian et al. |
| 7,014,652 B2 | 3/2006 | Cioanta et al. |
| 7,041,121 B1 | 5/2006 | Williams et al. |
| 7,066,935 B2 | 6/2006 | Swoyer et al. |
| 7,089,064 B2 | 8/2006 | Manker et al. |
| 7,130,697 B2 | 10/2006 | Chornenky et al. |
| 7,238,182 B2 | 7/2007 | Swoyer et al. |
| 7,247,155 B2 | 7/2007 | Hoey et al. |
| 7,261,709 B2 | 8/2007 | Swoyer et al. |
| 7,261,710 B2 | 8/2007 | Elmouelhi et al. |
| 7,322,974 B2 | 1/2008 | Swoyer et al. |
| 7,328,068 B2 | 2/2008 | Spinelli et al. |
| 7,328,069 B2 | 2/2008 | Gerber |
| 7,335,197 B2 | 2/2008 | Sage et al. |
| 7,340,300 B2 | 3/2008 | Christopherson et al. |
| 7,369,894 B2 | 5/2008 | Gerber |
| 7,429,262 B2 | 9/2008 | Woloszko et al. |
| 7,437,194 B2 | 10/2008 | Skwarek et al. |
| 7,470,228 B2 | 12/2008 | Connors et al. |
| 7,549,987 B2 | 6/2009 | Shadduck |
| 7,865,250 B2 | 1/2011 | Mrva et al. |
| 7,894,913 B2 | 2/2011 | Boggs et al. |
| 7,959,577 B2 | 6/2011 | Schmitz et al. |
| 8,048,069 B2 | 11/2011 | Skwarek et al. |
| 8,216,217 B2 | 7/2012 | Sharkey et al. |
| 8,244,327 B2 | 8/2012 | Fichtinger et al. |
| 8,251,985 B2 | 8/2012 | Hoey et al. |
| 8,272,383 B2 | 9/2012 | Hoey et al. |
| 8,273,079 B2 | 9/2012 | Hoey et al. |
| 8,301,264 B2 | 10/2012 | Achenbach et al. |
| 8,313,485 B2 | 11/2012 | Shadduck |
| 8,372,065 B2 | 2/2013 | Hoey et al. |
| 8,388,611 B2 | 3/2013 | Shadduck et al. |
| 8,409,109 B2 | 4/2013 | Tiesma et al. |
| 8,419,723 B2 | 4/2013 | Shadduck et al. |
| 8,550,743 B2 | 10/2013 | Bonde et al. |
| 8,585,692 B2 | 11/2013 | Shadduck et al. |
| 8,632,530 B2 | 1/2014 | Hoey et al. |
| 8,740,957 B2 | 6/2014 | Masotti |
| 8,801,702 B2 | 8/2014 | Hoey et al. |
| 8,900,223 B2 | 12/2014 | Shadduck |
| 9,198,708 B2 | 12/2015 | Hoey et al. |
| 2001/0037812 A1 * | 11/2001 | Dobak, III | A61B 18/02 128/898 |
| 2002/0078956 A1 | 6/2002 | Sharpe et al. |
| 2002/0111617 A1 | 8/2002 | Cosman et al. |
| 2002/0177846 A1 | 11/2002 | Mulier et al. |
| 2003/0069575 A1 | 4/2003 | Chin et al. |
| 2003/0092689 A1 | 5/2003 | Escandon et al. |
| 2003/0097126 A1 | 5/2003 | Woloszko et al. |
| 2003/0130575 A1 | 7/2003 | Desai |
| 2003/0206730 A1 | 11/2003 | Golan |
| 2004/0006334 A1 | 1/2004 | Beyar et al. |
| 2004/0068306 A1 | 4/2004 | Shadduck |
| 2004/0186422 A1 | 9/2004 | Rioux et al. |
| 2004/0230316 A1 | 11/2004 | Cioanta et al. |
| 2004/0267340 A1 | 12/2004 | Cioanta et al. |
| 2005/0096629 A1 | 5/2005 | Gerber et al. |
| 2005/0124915 A1 | 6/2005 | Eggers et al. |
| 2005/0149020 A1 | 7/2005 | Jahng |
| 2005/0159676 A1 | 7/2005 | Taylor et al. |
| 2006/0089636 A1 | 4/2006 | Christopherson et al. |
| 2006/0135955 A1 | 6/2006 | Shadduck |
| 2006/0178670 A1 | 8/2006 | Woloszko et al. |
| 2006/0224154 A1 | 10/2006 | Shadduck et al. |
| 2006/0224169 A1 | 10/2006 | Weisenburgh, II et al. |
| 2006/0253069 A1 | 11/2006 | Li et al. |
| 2006/0276871 A1 * | 12/2006 | Lamson | A61F 2/82 623/1.11 |
| 2007/0032785 A1 | 2/2007 | Diederich et al. |
| 2007/0038089 A1 | 2/2007 | Hatano et al. |
| 2007/0142846 A1 | 6/2007 | Catanese, III et al. |
| 2007/0179491 A1 | 8/2007 | Kratoska et al. |
| 2007/0197864 A1 | 8/2007 | Dejima et al. |
| 2007/0213703 A1 | 9/2007 | Naam et al. |
| 2008/0021445 A1 * | 1/2008 | Elmouelhi | A61B 18/1492 606/41 |
| 2008/0021484 A1 | 1/2008 | Catanese, III et al. |
| 2008/0021485 A1 | 1/2008 | Catanese, III et al. |
| 2008/0033232 A1 | 2/2008 | Catanese, III et al. |
| 2008/0033458 A1 | 2/2008 | McLean et al. |
| 2008/0033488 A1 | 2/2008 | Catanese, III et al. |
| 2008/0039833 A1 | 2/2008 | Catanese, III et al. |
| 2008/0039872 A1 | 2/2008 | Catanese, III et al. |
| 2008/0039874 A1 | 2/2008 | Catanese, III et al. |
| 2008/0039875 A1 | 2/2008 | Catanese, III et al. |
| 2008/0039876 A1 | 2/2008 | Catanese, III et al. |
| 2008/0039893 A1 | 2/2008 | McLean et al. |
| 2008/0039894 A1 | 2/2008 | Catanese, III et al. |
| 2008/0046045 A1 | 2/2008 | Yon et al. |
| 2008/0110457 A1 | 5/2008 | Barry et al. |
| 2008/0132826 A1 | 6/2008 | Shadduck et al. |
| 2008/0188811 A1 | 8/2008 | Kim |
| 2008/0208187 A1 | 8/2008 | Bhushan et al. |
| 2008/0214956 A1 | 9/2008 | Briggs et al. |
| 2008/0217325 A1 | 9/2008 | Von Buren et al. |
| 2008/0245375 A1 * | 10/2008 | Trudel | A61L 31/16 128/898 |
| 2008/0249399 A1 | 10/2008 | Appling et al. |
| 2008/0262491 A1 | 10/2008 | Swoyer et al. |
| 2008/0269737 A1 | 10/2008 | Elmouelhi et al. |
| 2008/0269862 A1 | 10/2008 | Elmouelhi et al. |
| 2008/0275440 A1 | 11/2008 | Kratoska et al. |
| 2008/0297287 A1 | 12/2008 | Shachar et al. |
| 2008/0312497 A1 | 12/2008 | Elmouelhi et al. |
| 2009/0018553 A1 | 1/2009 | McLean et al. |
| 2009/0054871 A1 | 2/2009 | Sharkey et al. |
| 2009/0138001 A1 | 5/2009 | Barry et al. |
| 2009/0149846 A1 | 6/2009 | Hoey et al. |
| 2009/0199855 A1 | 8/2009 | Davenport |
| 2009/0216220 A1 | 8/2009 | Hoey et al. |
| 2009/0227998 A1 | 9/2009 | Aljuri et al. |
| 2009/0306640 A1 | 12/2009 | Glaze et al. |
| 2010/0016757 A1 | 1/2010 | Greenburg et al. |
| 2010/0049031 A1 | 2/2010 | Fruland et al. |
| 2010/0094270 A1 | 4/2010 | Sharma |
| 2010/0114083 A1 | 5/2010 | Sharma |
| 2010/0145325 A1 * | 6/2010 | Hoey | A61B 18/04 606/27 |
| 2010/0179416 A1 | 7/2010 | Hoey et al. |
| 2010/0193568 A1 | 8/2010 | Scheib et al. |
| 2010/0204688 A1 | 8/2010 | Hoey et al. |
| 2010/0256636 A1 | 10/2010 | Fernandez et al. |
| 2010/0262133 A1 | 10/2010 | Hoey et al. |
| 2010/0262137 A1 | 10/2010 | Nye et al. |
| 2010/0286679 A1 | 11/2010 | Hoey et al. |
| 2010/0292767 A1 | 11/2010 | Hoey et al. |
| 2010/0298948 A1 | 11/2010 | Hoey et al. |
| 2011/0060328 A1 | 3/2011 | Skwarek et al. |
| 2011/0077628 A1 | 3/2011 | Hoey et al. |
| 2011/0106072 A1 | 5/2011 | Sundquist et al. |
| 2011/0160648 A1 | 6/2011 | Hoey |
| 2011/0264176 A1 | 10/2011 | Jackson et al. |
| 2011/0319759 A1 | 12/2011 | Liu et al. |
| 2012/0259271 A1 | 10/2012 | Shadduck et al. |

(56) References Cited

U.S. PATENT DOCUMENTS

| | | | |
|---|---|---|---|
| 2012/0265186 A1* | 10/2012 | Burger | A61B 17/8811 606/21 |
| 2012/0265276 A1 | 10/2012 | Curley | |
| 2012/0323167 A1 | 12/2012 | Hoey et al. | |
| 2013/0006231 A1* | 1/2013 | Sharma | A61B 5/1076 606/27 |
| 2013/0066308 A1 | 3/2013 | Landman | |
| 2013/0072855 A1 | 3/2013 | Sherry et al. | |
| 2013/0074847 A1 | 3/2013 | Hoey et al. | |
| 2013/0172867 A1 | 7/2013 | Shadduck et al. | |
| 2013/0261692 A1 | 10/2013 | Cardinal et al. | |
| 2014/0039356 A1 | 2/2014 | Sachs et al. | |
| 2014/0200568 A1 | 7/2014 | Sharma | |
| 2014/0276713 A1 | 9/2014 | Hoey et al. | |
| 2014/0288543 A1 | 9/2014 | Hoey et al. | |
| 2014/0354381 A1 | 12/2014 | Kohlhafer | |
| 2015/0025515 A1 | 1/2015 | Hoey et al. | |
| 2015/0025516 A1 | 1/2015 | Hoey et al. | |
| 2015/0126990 A1 | 5/2015 | Sharma et al. | |
| 2015/0157384 A1 | 6/2015 | Hoey et al. | |
| 2016/0081736 A1 | 3/2016 | Hoey et al. | |
| 2017/0056089 A1 | 3/2017 | Hoey et al. | |

FOREIGN PATENT DOCUMENTS

| | | |
|---|---|---|
| CN | 101072544 | 11/2007 |
| CN | 101257855 | 9/2008 |
| CN | 101006939 A | 11/2008 |
| CN | 101491458 A | 7/2009 |
| CN | 101803947 A | 8/2010 |
| JP | 7-507696 A | 8/1995 |
| JP | 8-501957 A | 3/1996 |
| JP | 8-504613 A | 5/1996 |
| JP | 11-318925 | 11/1999 |
| JP | 200014663 A | 1/2000 |
| JP | 2000005191 A | 1/2000 |
| JP | 2001500763 A | 1/2001 |
| JP | 2005137916 A | 6/2005 |
| WO | WO 92/10142 A1 | 6/1992 |
| WO | WO 01/24715 A1 | 4/2001 |
| WO | WO 03/088851 A1 | 10/2003 |
| WO | WO 03/096871 A2 | 11/2003 |
| WO | WO 2006/004482 A1 | 1/2006 |
| WO | WO 2008/083407 A1 | 7/2008 |
| WO | WO2010/080467 A2 | 7/2010 |
| WO | WO2013/160772 A2 | 10/2013 |
| WO | WO2015/089190 A1 | 6/2015 |
| WO | WO2017/106843 A1 | 6/2017 |

OTHER PUBLICATIONS

Colin, Pierre, Focal Laser Ablation of Prostate Cancer: Definition, Needs, and Future, Mar. 14, 2012, Hindawi Publishing Company, Advances in Urology, vol. 2012, Article ID 589160.*

Hai; Photoselective Vaporization Prostatectomy: A Palliative Treatment Option for Men with Urinary Obstruction Secondary to Prostate Cancer; PCRI Prost.Cancer Rsrch.Inst. Reprint.from PCRI Insights Nov. 2005, vol. 8(4); Dwnld from http://www.prostate-cancer.org/pericms/node/233 on May 10, 2012; 4 pages.

Nguyen et al; Updated results of magnetic resonance imaging guided partial prostate brachytherapy for favorable risk prostate cancer: implications for focal therapy; J. Urol.; 188(4); pp. 1151-1156; Oct. 2012.

Hoey et al.; U.S. Appl. No. 15/851,333 entitled "Vapor ablation systems and methods," filed Dec. 21, 2017.

Hoey et al.; U.S. Appl. No. 15/864,957 entitled "Transperineal Vapor ablation systems and methods," filed Jan. 8, 2018.

Hoey et al.; U.S. Appl. No. 15/900,295 entitled "Systems and methods for prostate treatment," filed Feb. 20, 2018

Hastings et al.; U.S. Appl. No. 15/011,005 entitled "Vapor ablation systems and methods," filed Jan. 29, 2016.

Hastings et al.; U.S. Appl. No. 15/035,944 entitled "Vapor ablation systems and methods," filed May 11, 2016.

Hoey et al.; U.S. Appl. No. 15/154,536 entitled "Systems and methods for treating the bladder with condensable vapor," filed May 13, 2016.

* cited by examiner

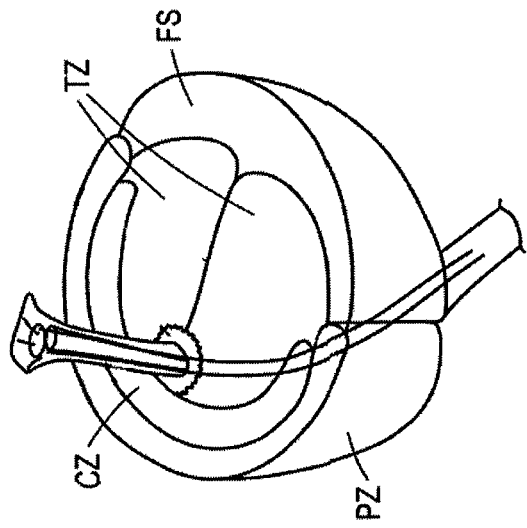
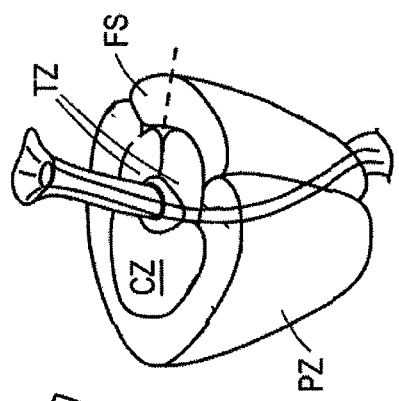
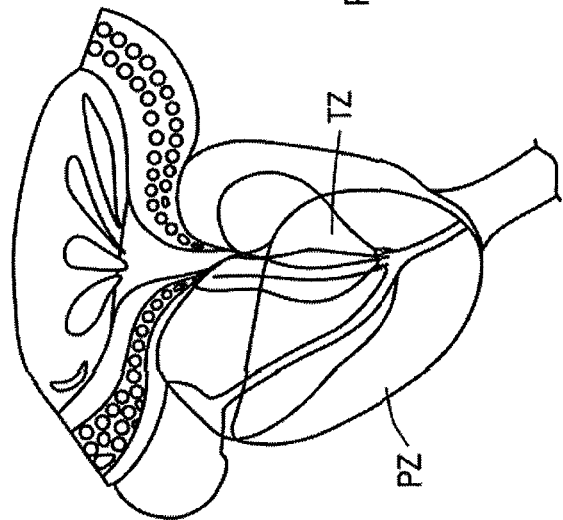
FIG. 2C
FIG. 2B
FIG. 2A

SYSTEMS AND METHODS FOR TREATING PROSTATE CANCER

CROSS REFERENCES TO RELATED APPLICATIONS

This Application claims the benefit of US Provisional Patent Application No. 61/785,649, filed Mar. 14, 2013, titled "SYSTEMS AND METHODS FOR TREATING PROSTATE CANCER", which is incorporated by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The present invention relates to devices and related methods for treatment of prostate tissue, and more specifically treatment of prostate cancer with heated condensable vapor.

BACKGROUND

The prostate early in life is the size and shape of a walnut and prior to the enlargement resulting from benign prostatic hyperplasia, weighs about 20 grams. Prostate enlargement appears to be a normal process. With age, the prostate gradually increases in size to twice or more its normal size. The fibromuscular tissue of the outer prostatic capsule restricts expansion after the gland reaches a certain size. Because of such restriction on expansion, the intracapsular tissue will compress against and constrict the prostatic urethra, thus causing resistance to urine flow.

FIG. 1 is a sectional schematic view the male urogenital anatomy, with the walnut-sized prostate 100 located below the bladder 105 and bladder neck 106. The walls 108 of bladder 105 can expand and contract to cause urine flow through the urethra 110, which extends from the bladder 105, through the prostate 100 and penis 112. The portion of urethra 110 that is surrounded by the prostate 100 can be referred to as the prostatic urethra 120. The prostate 100 also surrounds the ejaculatory duct 122 which have an open termination in the prostatic urethra 120. During sexual arousal, sperm is transported from the testes 124 by the ductus deferens 126 to the prostate 100 which provides fluids that combine with sperm to form semen during ejaculation. On each side of the prostate, the ductus deferens 126 and seminal vesicles 128 join to form a single tube called an ejaculatory duct 122. Thus, each ejaculatory duct 122 carries the seminal vesicle secretions and sperm into the prostatic urethra 120. Also shown in FIG. 1 are Cowper's Gland 130, the Sigmoid Colon 132, the Rectum 134, and Epididymis 136.

Referring to FIGS. 2A-2C, the prostate can be classified into three zones: the peripheral zone, transition zone, and central zone. Peripheral zone (PZ) comprises about 70% of the volume of a male's prostate. This sub-capsular portion of the posterior aspect of the prostate gland surrounds the distal urethra and 70 to 80% of cancers originate in the peripheral zone tissue. The central zone (CZ) surrounds the ejaculatory ducts and contains about 20-25% of the prostate volume. The central zone is often the site of inflammatory processes.

The transition zone (TZ) is the site in which benign prostatic hyperplasia develops, and contains about 5-10% of the volume of glandular elements in a normal prostate, but can constitute up to 80% of such volume in cases of BPH. The transition zone includes two lateral prostate lobes and the periurethral gland region. As can be understood from FIGS. 2A-2C, there are natural barriers around the transition zone, i.e., the prostatic urethra, the anterior fibromuscular stroma FS, and a fibrous plane FP between the transition zone and peripheral zone. In FIGS. 2A-2C, the anterior fibromuscular stroma FS or fibromuscular zone can be seen and is predominantly fibromuscular tissue.

Approximately 70% to 80% of prostate cancers originate in the peripheral zone of the prostate and may be confined to the peripheral zone. In recent years, there has been an increased interest in focal therapy for prostate cancer, treating only regions of tissue in which cancer has been found following biopsies. Prior art focal therapy treatments, such as with RF ablation energy, may not confine the treatment to the peripheral zone tissue.

SUMMARY OF THE DISCLOSURE

In some embodiments, a method for treating a patient suffering from prostate cancer is provided, comprising the insertion of a vapor delivery needle through into at least one location in peripheral zone tissue, delivering condensable vapor through the needle into the peripheral zone tissue, and ablating either a focal region of such peripheral zone tissue or the entire peripheral zone which is surrounded by a pseudo-capsule of dense tissue.

A method for treating abnormal prostate tissue is provided, comprising introducing a vapor delivery needle into peripheral zone tissue of a human prostate, and delivering condensable vapor through the needle to ablate peripheral zone tissue without ablating non-peripheral zone tissue.

In some embodiments, the introducing step includes introducing the needle into peripheral zone tissue within first and second prostate lobes.

In other embodiments, the introducing step includes positioning the needle in a plurality of locations in the peripheral zone tissue prior to delivering condensable vapor.

In some embodiments, the peripheral zone tissue includes malignant tissue.

In one embodiment, the introducing step includes introducing the needle in at least one of a perineal approach, trans-rectal approach or trans-urethral approach.

In some embodiments, the introducing step includes positioning the needle under imaging guidance. In some embodiments, the imaging guidance is ultrasound or MRI.

In one embodiment, the condensable vapor includes water vapor.

In some embodiments, the delivering step includes vaporizing a flow of fluid having a flow rate ranging from 1 cc/min to 60 cc/min to thereby provide the condensable vapor.

In one embodiment, the delivering step includes delivering condensable vapor configured for focal ablation of abnormal tissue.

In some embodiments, the condensable vapor is delivered for between 2 seconds and 20 seconds at each focal ablation site.

In some embodiments, the delivered condensable vapor is configured to deliver less than 150 calories for each focal ablation site.

In other embodiments, the delivering step includes delivering condensable vapor configured for non-focal ablation of abnormal tissue.

In some embodiments, the delivering step includes delivering condensable vapor configured for ablation of substantially all peripheral zone tissue in a lobe.

In alternative embodiments, the condensable vapor is delivered for between 10 seconds and 40 seconds at each peripheral zone lobe.

In some embodiments, the delivered condensable vapor is configured to deliver between 150 and 300 calories for each peripheral zone lobe.

In one embodiment, the delivery of vapor is configured with pressure and flow parameters that result in the condensable vapor being reflected by barrier tissue surrounding the peripheral zone tissue.

In other embodiments, the method further comprises insulating tissue outside of the prostate from the needle during the delivering step. In one embodiment, the insulating step comprises insulating the needle with an active cooling system. In another embodiment, the insulating step comprises insulating the needle with a vacuum system. In an alternative embodiment, the insulating step comprises insulating the needle with an insulating sheath.

A method for treating prostate cancer is provided, comprising introducing a needle into peripheral zone lobe in a prostate, and delivering vapor through the needle at pressure and flow parameters that result in the condensable vapor being reflected by barrier tissue surrounding the peripheral zone lobe to thereby ablate the peripheral zone lobe without ablating non-peripheral zone tissue.

Another method for treating prostate cancer is provided, comprising delivering vapor into peripheral zone lobe in a prostate, wherein the vapor is configured to deliver between 300 and 1000 calories to the peripheral zone lobe to thereby ablate malignant tissue.

In some embodiments, the volume of vapor is adapted for ablation of the entire peripheral zone lobe.

An additional method for treating prostate cancer is provided, comprising positioning a needle into peripheral zone lobe in a prostate, and delivering vapor into the peripheral zone lobe, wherein the vapor is configured to deliver less than 150 calories to a site in the peripheral zone lobe to thereby cause focal ablation of malignant tissue in the peripheral zone lobe.

In some embodiments, the volume of vapor is adapted for said focal ablation.

In some embodiments, the method further comprises re-positioning the needle in the peripheral zone lobe and repeating the delivering step at a second site to cause a second focal ablation of malignant tissue in the peripheral zone.

In one embodiment, the method further comprises measuring a temperature of the prostate, and terminating delivery of the condensable vapor when the temperature of the prostate reaches a pre-determined threshold. In another embodiment, the measuring step comprises measuring a temperature of an outer capsule of the prostate. In some embodiments, the pre-determined threshold comprises between 44-60 degrees C.

The method can further comprise withdrawing the needle from the prostate to seal a prostate capsule and prevent seeding into non-prostate tissue. In some embodiments, the method comprises releasing a flow of condensable vapor during the withdrawing step.

A prostate cancer therapy system is provided, comprising a vapor generator, and a vapor delivery needle coupled to the vapor generator, the vapor delivery needle configured to be inserted into a peripheral zone of a prostate to deliver vapor to the peripheral zone to treat prostate cancer.

In some embodiments, the vapor generator comprises a controller configured to deliver between 1 and 150 calories of vapor into the peripheral zone.

In other embodiments, the vapor generator comprises a controller configured to deliver between 150 and 300 calories of vapor into the peripheral zone.

In some embodiments, the vapor generator comprises a controller configured to deliver between 300 and 1,000 calories of vapor into the peripheral zone.

In another embodiment, the vapor generator is disposed within a handle of the vapor delivery needle.

In another embodiment, the vapor delivery needle includes a plurality of vapor ports.

In some embodiments, the vapor delivery needle further comprises a vacuum sleeve configured to protect tissue outside of the prostate.

BRIEF DESCRIPTION OF THE DRAWINGS

In order to better understand the invention and to see how it may be carried out in practice, some preferred embodiments are next described, by way of non-limiting examples only, with reference to the accompanying drawings, in which like reference characters denote corresponding features consistently throughout similar embodiments in the attached drawings.

FIGS. 2A-2C are views of a patient's prostate showing zones of prostate tissue.

DETAILED DESCRIPTION OF THE INVENTION

This disclosure generally provides systems and methods for delivering a heated vapor to tissue to ablate the tissue. In some embodiments, a vapor delivery system can be provided which can be configured to deliver vapor to tissue to ablate and destroy cancerous tissue. Systems and methods provided herein can be specifically tailored for providing vapor to prostate tissue to ablate the prostate tissue, including cancerous tissues and cells located in the prostate.

In some embodiments, a vapor delivery system can include a needle-like vapor delivery device adapted and configured to access a prostate of a male patient. The needle can be inserted into the prostate trans-perineally, trans-rectally, or trans-abdominally, for example. Vapor can be generated in a vapor generator disposed inside the device, or coupled to the device, and can be delivered through the device into the prostate to ablate the tissue. In another embodiment, the vapor delivery device can be configured to access the prostate trans-urethrally to deliver vapor to the prostate. Specific methods and treatment parameters for prostate cancer therapy with a vapor delivery device will also be discussed.

Figure 1:
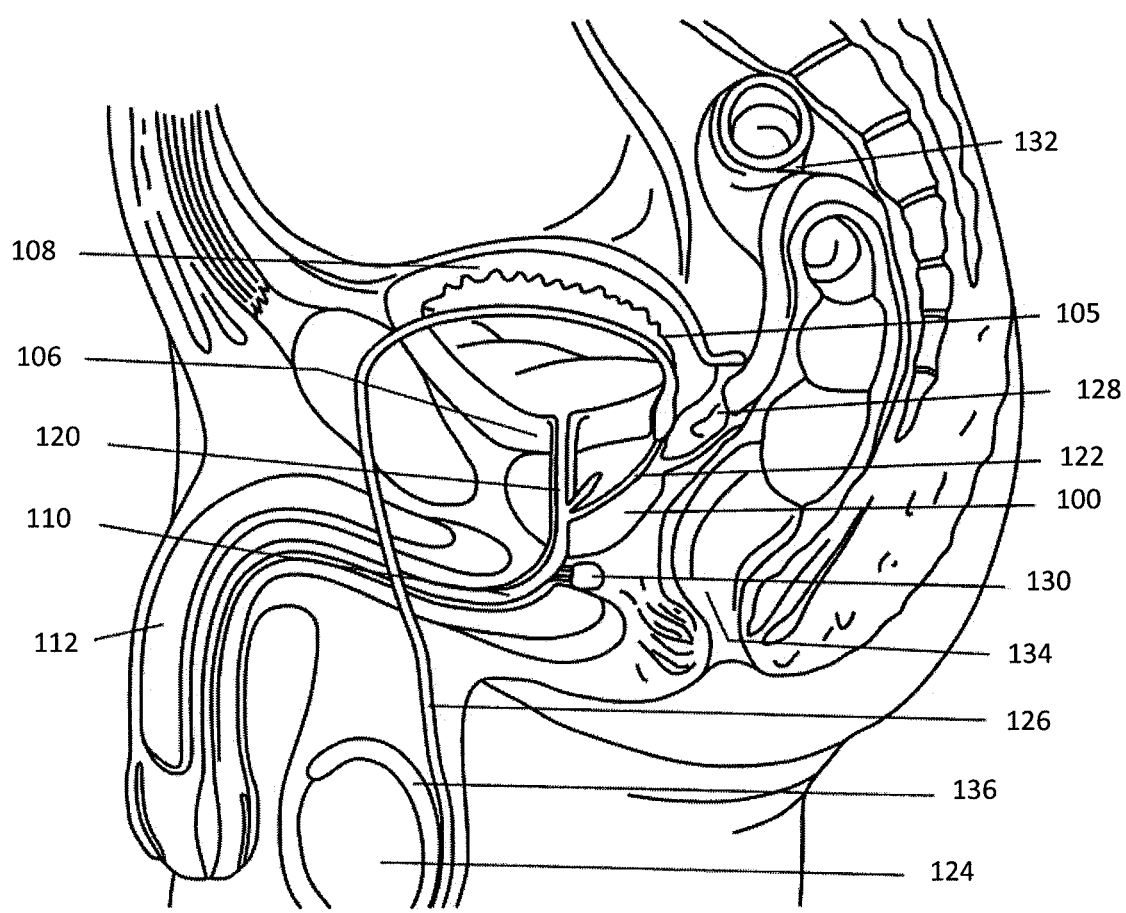
FIG. 1 is a sectional schematic view the male urogenital anatomy.
Figure 3:
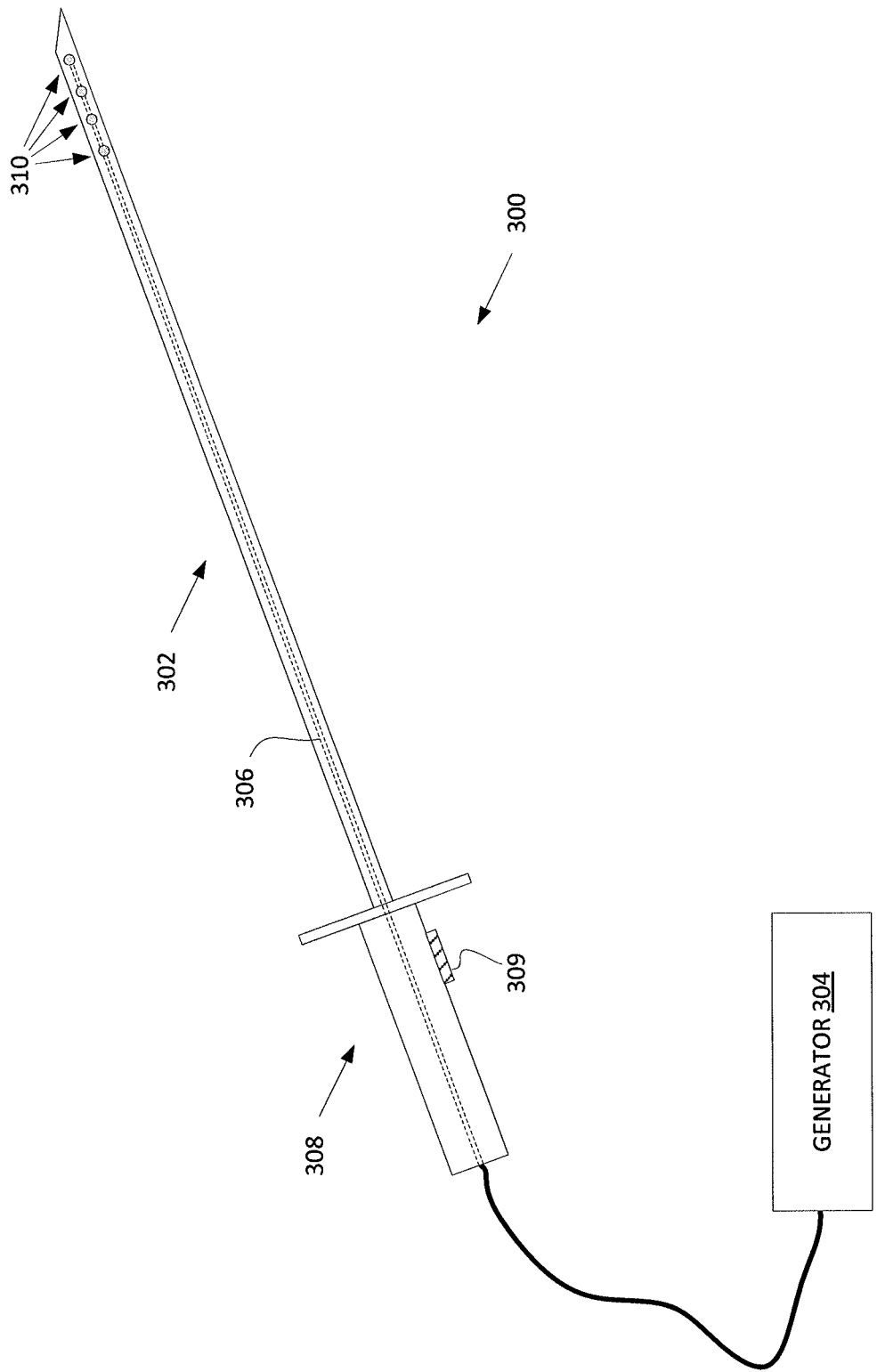
FIG. 3 shows one embodiment of a vapor delivery system.

FIG. 3 illustrates one embodiment of a vapor delivery device 300 comprising a vapor delivery needle 302. The vapor delivery needle 302 can comprise a rigid shaft made of a material commonly used in medical devices, such as stainless steel, titanium, nitinol, polymer, or the like. In some embodiments, the vapor delivery needle can be a 12-20 gauge needle. In some embodiments, the vapor delivery needle can include a tissue piercing distal tip, as shown. The vapor delivery device 300 can be connected to a vapor generator 304, which can be configured to generate a heated condensable vapor and deliver the vapor to the vapor delivery device. The vapor generator can introduce vapor into a vapor lumen 306 of the vapor delivery device. The vapor lumen can extend along a length of the vapor delivery device, including along a handle portion 308 and through the vapor delivery needle 302.

The vapor delivery needle 302 can include one or more vapor delivery ports 310 that permit passage of vapor from the vapor lumen from the vapor delivery needle. In one embodiment, and end of the vapor delivery needle can be a vapor delivery port (like the end of a hose). The vapor delivery ports can have diameters ranging from 0.006 to 0.020". In some embodiments, the vapor delivery ports can be arranged along a distal portion of the vapor delivery needle, at the end portion of the vapor lumen. The vapor delivery needle can have any suitable diameter with a plurality of vapor ports extending over an axial length of 1 mm to 20 mm. In another embodiment, the vapor ports can extend over an axial length of 0.1 mm to 60 mm. In some embodiments, individual vapor ports can be spaced from 0.5 mm to 5 mm apart. In one embodiment, the vapor ports can be radially symmetric to direct the flow of vapor uniformly about the distal portion of the needle into prostate tissue. In another embodiment, the vapor ports can be radially asymmetric to direct the flow of vapor to one side of the needle, for example to direct the vapor flow inwardly in the prostate tissue and away from the outer prostate capsule. In such an embodiment, the handle and/or proximal needle shaft (not shown) can be configured with markings that indicate the radial orientation of vapor ports. In some embodiments, the vapor delivery ports can be of a uniform shape and size. However, in other embodiments, the ports can include varying shapes and sizes. For example, in one embodiment, ports towards a proximal end of the vapor delivery needle can be larger than ports towards a distal end of the vapor delivery needle.

The vapor delivery device can further include a controller that can be configured to control the various parameters of vapor delivery. For example, the controller can be configured to control the generation of vapor including a selected vapor quality, can be configured to deliver vapor for a selected treatment interval, and a selected pressure. The controller can be incorporated into the generator, for example, or can be a separate controller module apart from the generator. The handle portion 308 of the device can include a button or control feature 309 that can be actuated to control operation of the device. For example, pushing the button can turn on the device and begin the delivery of vapor.

The vapor generator provided can be used to generate and control delivery of a condensable vapor through the vapor delivery device to ablate tissue. The vapor generator can be configured to generate and deliver a vapor media that has a precisely controlled quality to provide a precise amount of thermal energy delivery, for example measured in calories per second. Descriptions of suitable vapor generators can be found in the following U.S. patent application Ser. Nos. 61/068,130; 61/191,459; 61/112,097; 61/112,099; 61/112,103; 12/389,808; 12/555,635, all of which are incorporated herein by reference.

Figure 4:
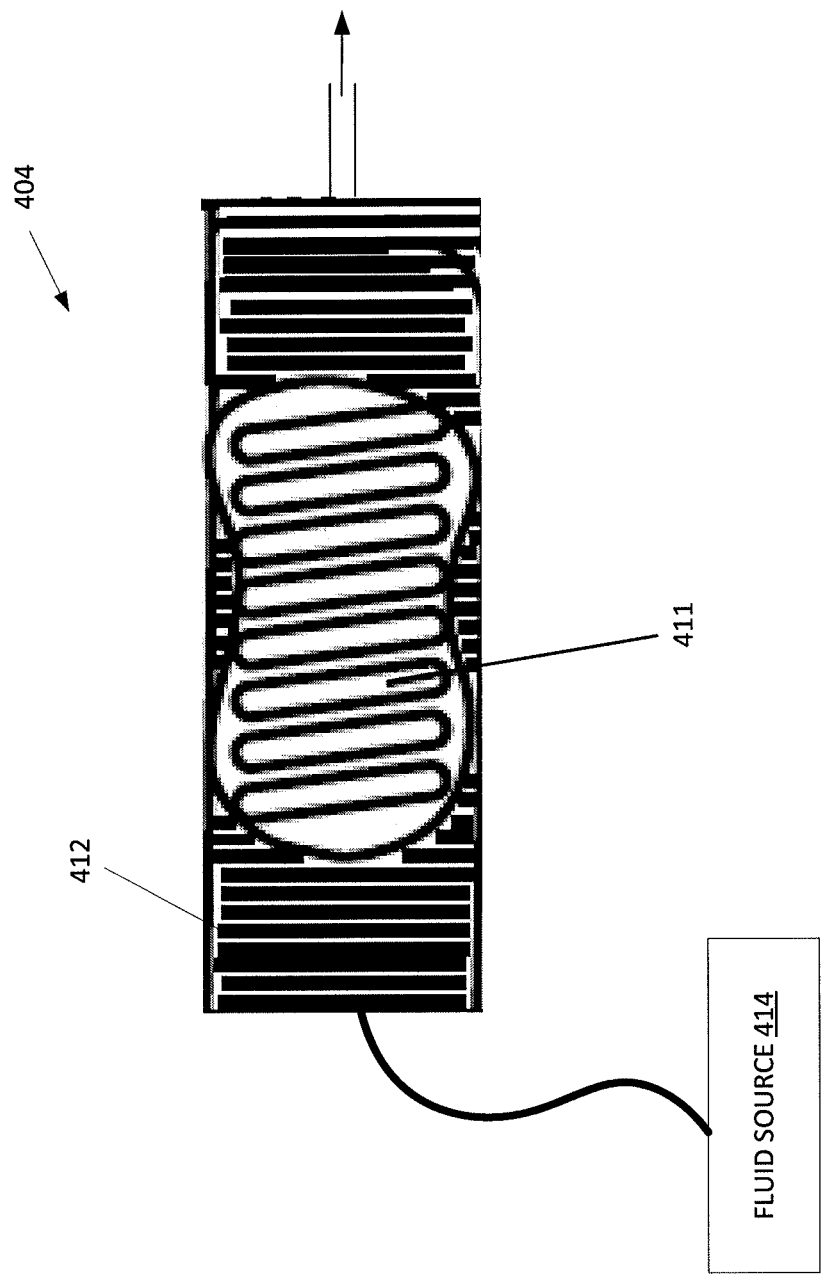
FIG. 4 is one embodiment of a vapor generator.

FIG. 4 illustrates is a cutaway view of an inductive vapor generator 404 that can be used with the vapor delivery systems described herein. The inductive vapor generator can comprise a helically coiled tube or pipe 411 surrounded by a coil of electrical wire 412. The helically coiled tube 411 can be seen through the cutaway section of FIG. 4. The coiled tube or pipe 411 can be connected to a fluid source 414, which can introduce fluid into the coiled tube or pipe. Electrical energy can be applied to the electrical wire to inductively heat the coiled tube to generate a heated condensable vapor from the fluid inside the inductive vapor generator. The fluid flow in the helical tube or pipe can be converted to vapor instantly with the application of electrical energy to the electrical wire. The condensable vapor can then exit the vapor generator as shown.

Figure 5:
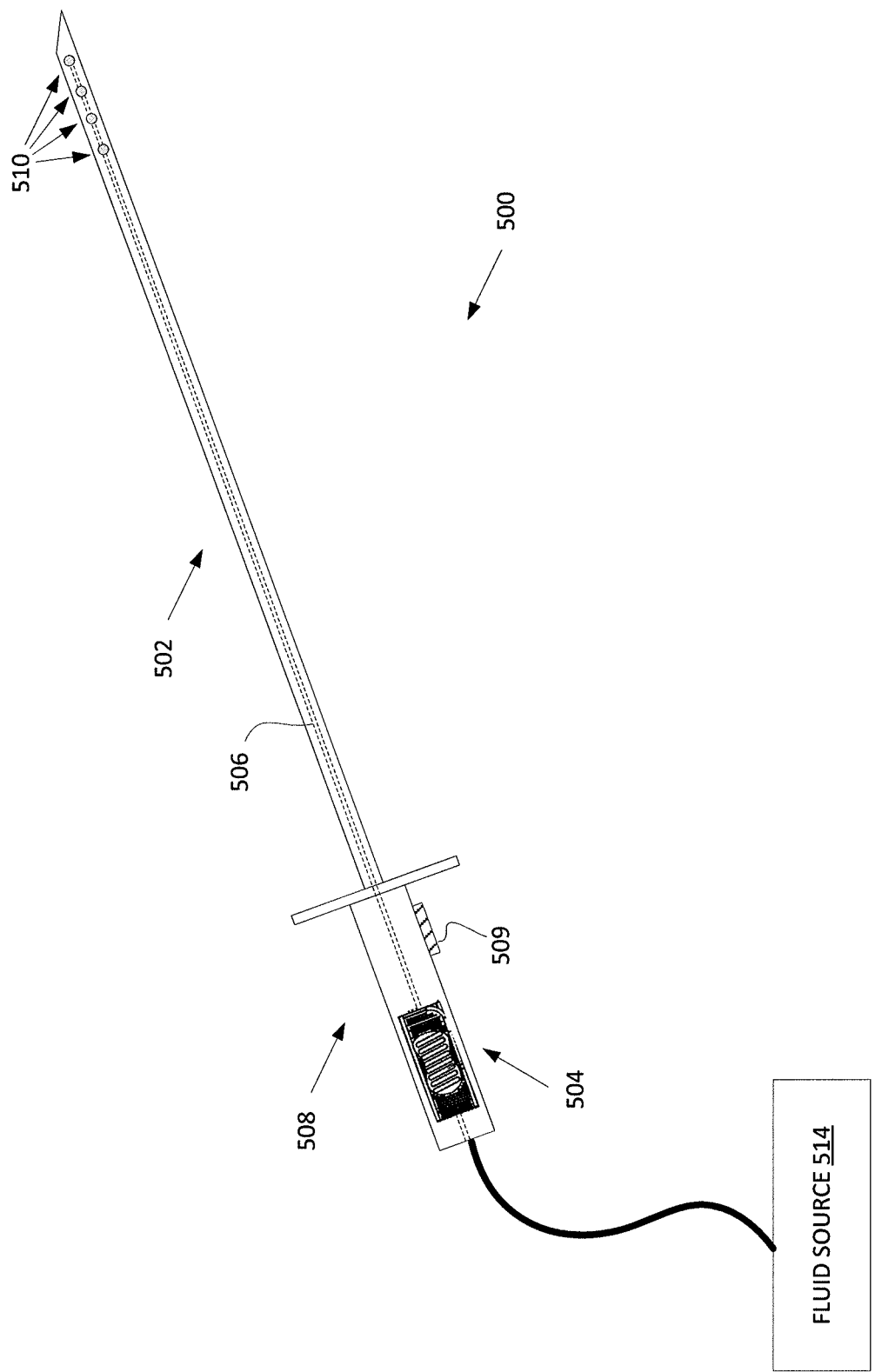
FIG. 5 is another embodiment of a vapor delivery system.

FIG. 5 shows another embodiment of a vapor delivery device 500. The vapor delivery device is similar to the device shown in FIG. 3, and includes a vapor delivery needle 502, vapor lumen 506, handle portion 508, button 509, and vapor delivery ports 510. The vapor delivery system of FIG. 5, however, includes the vapor generator 504 incorporated into the device itself, such as into the handle as shown. The vapor generator 504 can receive fluid from a fluid source 514, as shown, or alternatively, a pre-determined amount of fluid can be loaded into the generator or the vapor delivery system prior to therapy.

Figure 6A:
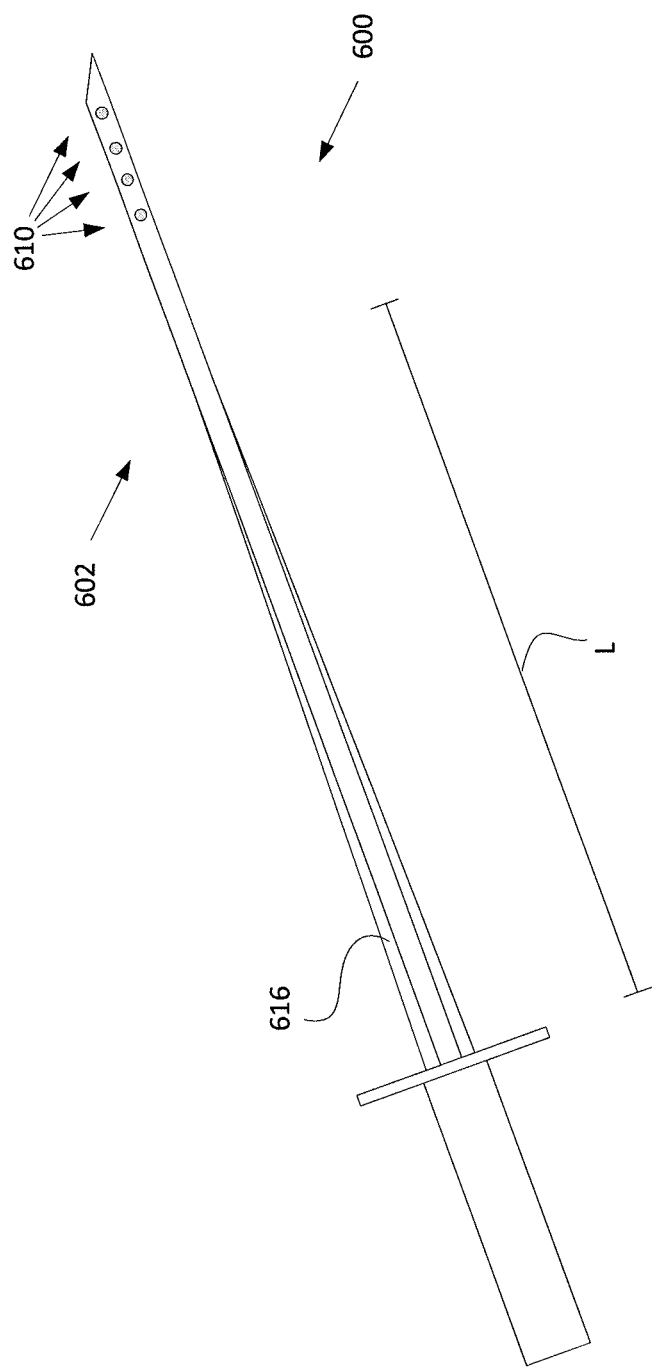
FIGS. 6A-6B illustrate embodiments of an insulating layer for a vapor delivery system.

FIG. 6A shows a cutaway view of a vapor delivery device 600 including an insulating layer 616 surrounding at least a portion of the vapor delivery needle 602. The insulating layer 616 can comprise, for example, an insulating material with a low thermal conductivity, or alternatively, can comprise a vacuum channel or vacuum sleeve, or an active cooling system comprising a channel filled with a gas or other insulating medium such as a fluid. In FIG. 6A, the insulating layer 616 can extend along a length L of the vapor delivery needle. In some embodiments, the insulating layer 616 can be tapered so as to reduce in thickness as the layer gets closer to the vapor delivery ports 610 of the vapor delivery needle. The tapered layer can aid in reducing trauma to tissue when the needle is inserted into tissue. The tapered layer may also form a seal with the tissue that prevents vapor from escaping from the needle entrance hole. In some embodiments, the length of the insulating layer can be chosen depending on the target tissue to be ablated. For example, if the vapor delivery device is intended to deliver vapor trans-perineally to prostate tissue, the length L of the insulating layer can be chosen so as to thermally protect and insulate the intervening tissues between the perineum and the prostate of the patient.

Figure 6B:
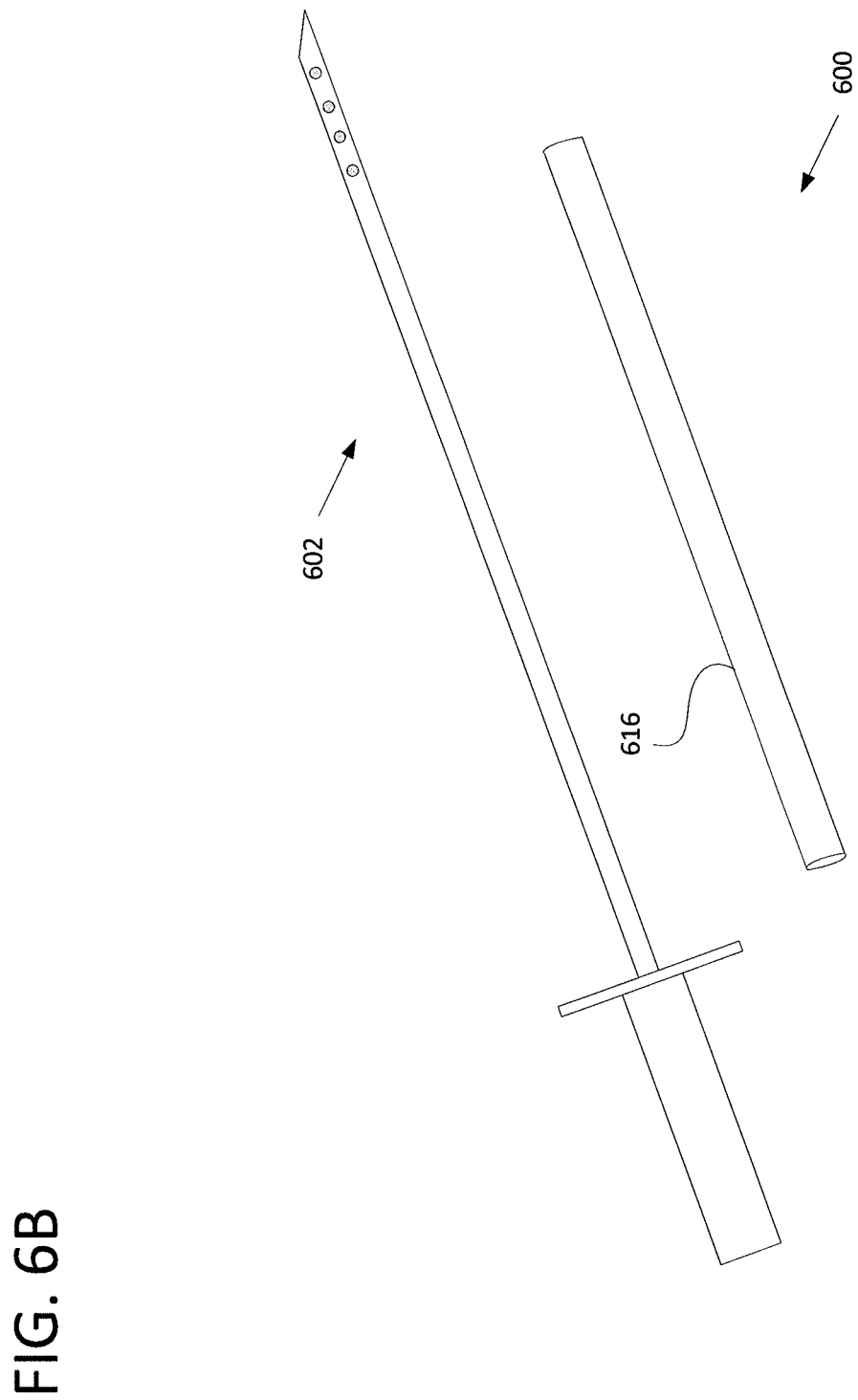

FIG. 6B shows another embodiment of an insulating layer 616 for use with a vapor delivery device 600. The insulating layer 616 of FIG. 6B can be a removable sheath that can slide over the vapor delivery needle 602. In one embodiment, the insulating layer can comprise a vacuum sheath in which a pair of concentric tubes are attached or connected together and a vacuum is created between the tubes. The insulating layer can then be inserted over the vapor delivery needle to protect tissue from being heated by coming into contact directly with the vapor delivery needle.

Figure 7:
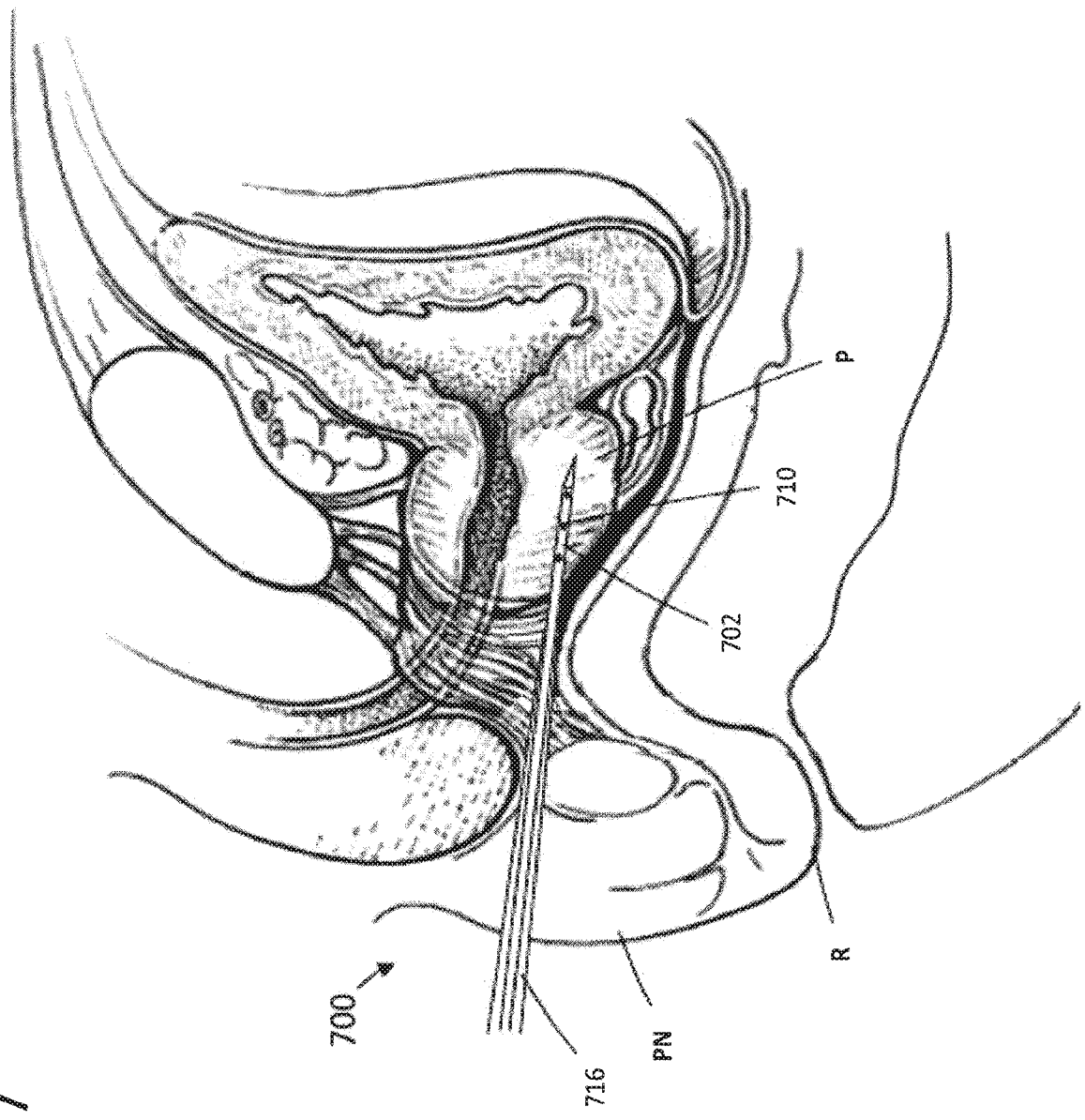
FIG. 7 shows one embodiment of a vapor delivery system for treating prostate cancer.

FIG. 7 shows one method for treating prostate cancer with the vapor delivery devices described herein. Injection of a heated condensable vapor, for approximately 1 to 20 seconds, can be used for focal ablation of cancerous prostate tissue. Furthermore, injection of vapor media at selected flow rates will not propagate beyond the pseudo-capsule or denser tissue surrounding various regions of the prostate, such as the peripheral zone, thus allowing ablation of a targeted region of the prostate without ablation of adjacent zone tissue. In particular, nerve tissue residing on the outside of the prostate capsule will not be exposed to vapor, and will not be ablated, thereby reducing or eliminating the incidence of incontinence or sexual dis-function.

In one embodiment, a vapor delivery device 700 including a vapor delivery needle 702 can be positioned in one or more locations the prostate, and can be configured to deliver injections of vapor ranging from 1-20 seconds in each location. In one specific embodiment, vapor can be delivered into the prostate for 9-12 seconds. In the embodiment illustrated in FIG. 7, the vapor delivery needle can be inserted trans-perineally into the prostate. In some embodiments, the vapor delivery needle can be inserted into a peripheral zone of the prostate to deliver vapor to the peripheral zone. The needle can be placed in multiple paths in the peripheral zone tissue.

FIG. 7 illustrates schematically a vapor delivery device 700 with vapor delivery needle 702 being introduced through the patient's perineum PN spaced apart from rectum R into the patient's prostate P. The system 700 can be configured to deliver condensable vapor from the needle to the prostate through vapor delivery ports 710. Also shown in FIG. 7 is an insulating layer 716, as described above, which can be included around the needle to insulate intervening tissues from heat emanating from the needle.

Figure 8:
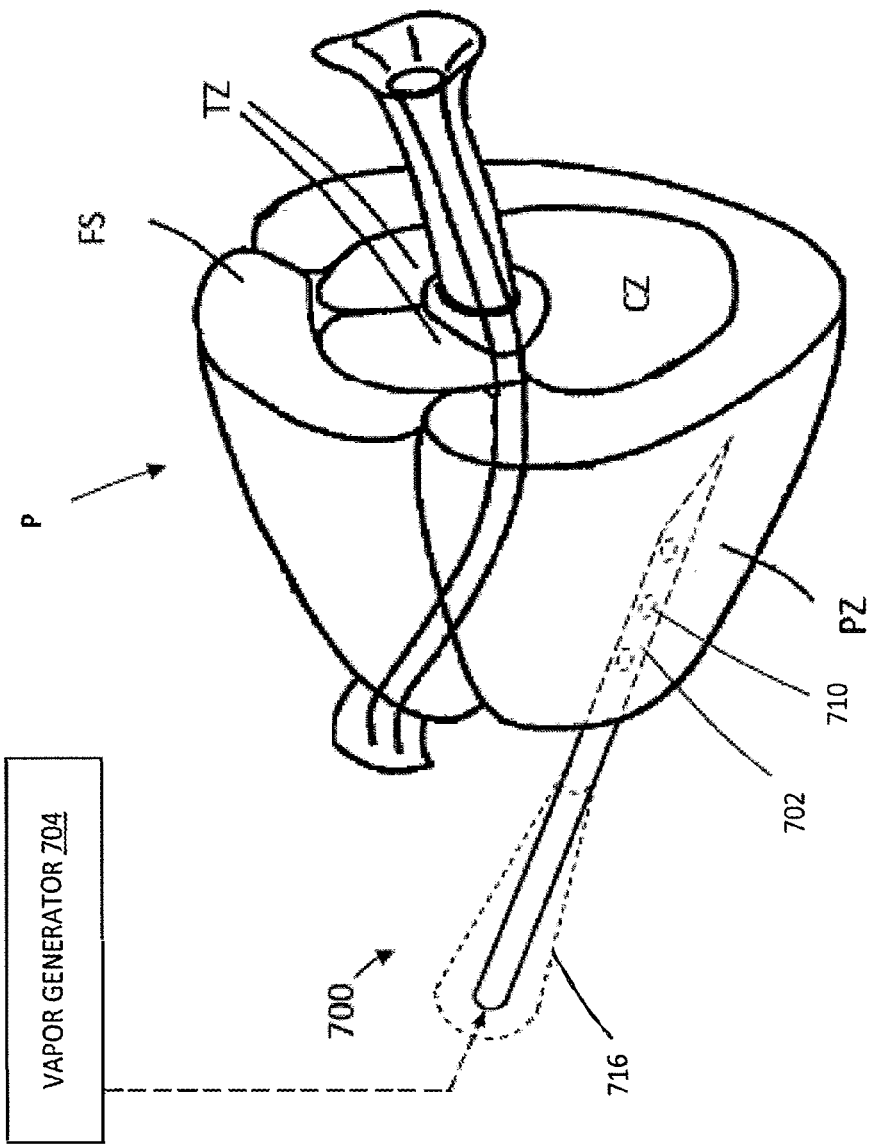
FIG. 8 is a sectional view of a patient's prostate showing a method delivering ablative vapor to a patient's prostate to ablate peripheral zone tissue which is malignant.

FIG. 8 is an enlarged schematic view showing the vapor delivery needle being introduced into the prostate P. In this specific illustrative embodiment, the needle is being inserted into the peripheral zone PZ. However, in other embodiments the needle can be inserted into the other regions of the prostate, including the central zone CZ, the transition zone TZ, or the fibromuscular stroma FS. As described above, the vapor delivery system can be connected to a vapor generator 704 communicating with the vapor delivery needle. The needle 702 can include an insulating layer or sheath 716 to prevent the needle shaft from heating tissue along the path of the needle outside of the prostate, with the needle optionally being extendable from the insulating layer. In some embodiments, the insulating layer can comprise an active cooling or vacuum insulation layer.

In general, a method corresponding to treatment of prostate cancer comprises introducing a needle into prostate tissue, and delivering vapor through the needle to ablate prostate tissue. In one specific embodiment, the method can comprise inserting the needle into peripheral zone tissue of the prostate, and delivering vapor through the needle to ablate peripheral zone tissue of the prostate without ablating non-peripheral zone tissue of the prostate. The method can include introducing the vapor delivery needle into both the first and second prostate lobes. The method can also include positioning the needle in a plurality of locations in the prostate tissue prior to delivering vapor into the prostate. In some embodiments, the method can include introducing the needle under imaging guidance such as ultrasound guidance. Vapor entering the prostate has a lower density than surrounding tissue, thereby showing up as a brighter region in an ultrasound image. Real time ultrasound imaging, such as TRUS (Trans-Rectal-Ultrasound), can be used to image vapor entering the prostate from a trans-perineum or trans-urethral needle placement.

In one embodiment, a method of treating prostate cancer can comprise delivering vapor from vapor delivery needle having a plurality of vapor delivery ports to ablate prostate tissue and form a plurality of lesions in the prostate. Lesions in tissue can be determined by treatment and dosing. Focal lesions can be lesions having a size of 1-10 mm, and can be created by delivering less than 150 calories of vapor into the tissue, or by delivering vapor from 2-20 seconds. Regional lesions can be lesions having a size greater than 10 mm, and can be created by delivering between 150-300 calories of vapor into the tissue, or by delivering vapor from 10-40 seconds. Zonal lesions can be lesions that cover a majority (e.g., greater than 75%) of a specified zone of prostate tissue (e.g., peripheral zone), and can be created by delivering between 300-1000 calories of vapor into the tissue, or by delivering vapor from 20-60 seconds.

In one embodiment, the method includes the injection of condensable vapor, and more particularly the vapor delivery step includes vaporizing a flow of fluid having a flow rate ranging from 1 cc/min to 60 cc/min to thereby provide the condensable vapor. The method can include injecting vapor media for between 1-20 seconds for a focal ablation site. The delivered vapor media can be configured to deliver less than 150 calories for a focal ablation site. The method can include delivering vapor media configured for regional ablation of abnormal tissue, wherein the vapor media is configured to deliver between 150 and 300 calories for each peripheral zone lobe. The method can include delivering vapor media configured for zonal ablation of abnormal tissue, wherein the vapor media is configured to deliver between 300 and 1000 calories for each peripheral zone lobe.

In another embodiment, the vapor media can be injected into peripheral zone tissue at pressure and flow parameters that result in the vapor media being reflected by barrier tissue surrounding the peripheral zone lobe to thereby ablate said lobe without ablating non-peripheral zone tissue. A method for treating prostate cancer comprises delivering vapor media into peripheral zone lobe in a prostate, wherein the vapor media is configured to deliver between 40 and 800 calories to the peripheral zone lobe to thereby ablate malignant tissue with the volume of vapor media being adapted for ablation of the entire peripheral zone lobe. Another method comprises delivering vapor media into peripheral zone lobe in a prostate wherein the vapor media is configured to deliver less than 150 calories to a site in the peripheral zone lobe to thereby cause focal ablation of malignant tissue.

Figure 9:
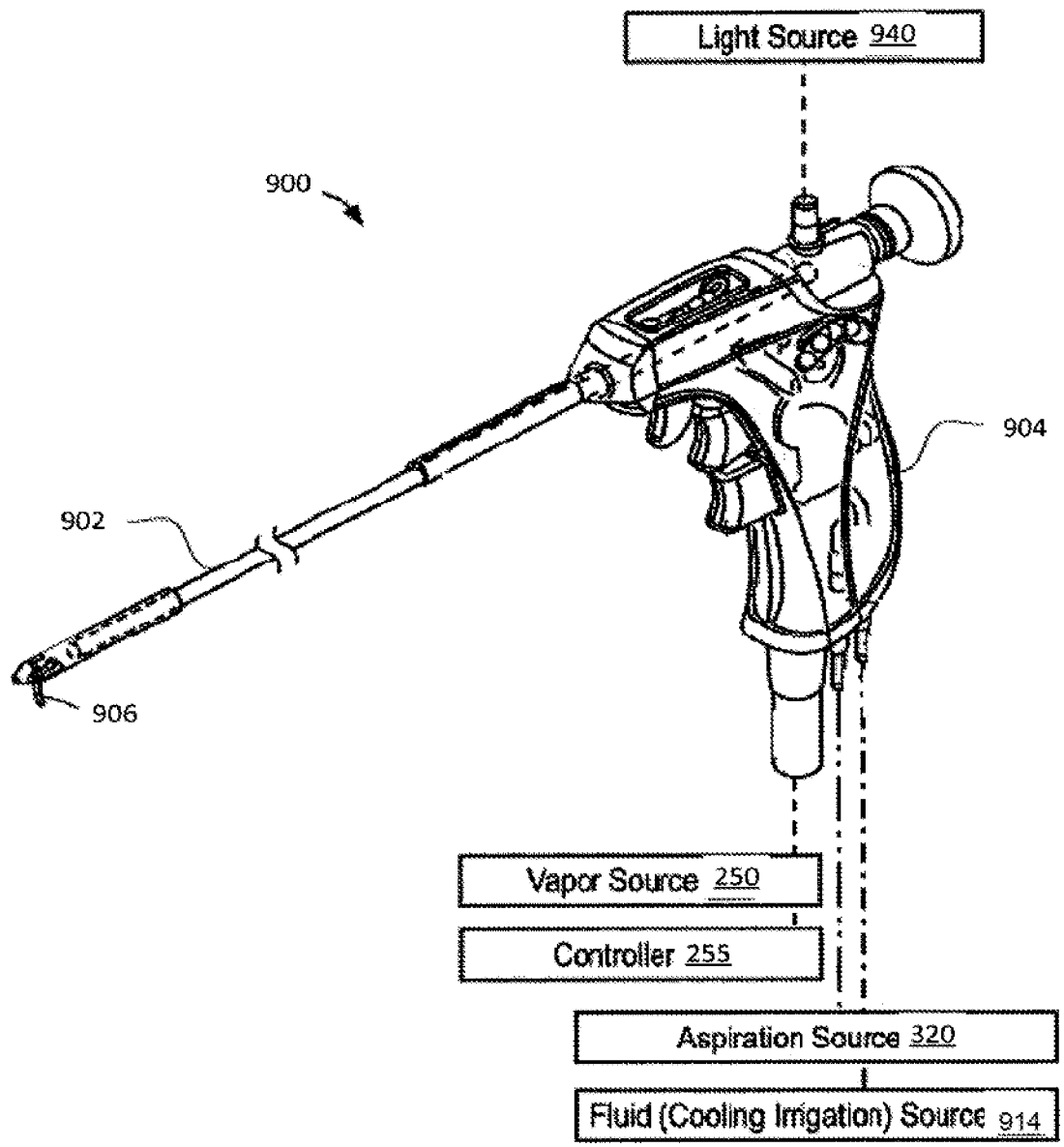
FIG. 9 shows a trans-urethral vapor delivery system.

FIG. 9 shows one embodiment of a vapor delivery device 900 configured to access the prostate trans-urethrally. Vapor delivery device 900 can have an elongate shaft 902 configured for insertion into the urethra of a patient and a handle portion 904 for gripping with a human hand. The vapor device 900 can include a vapor delivery needle 906 configured to extend from a distal portion of the elongate shaft 902. The vapor delivery needle can extend generally perpendicular to or transverse from the shaft, and can include one or more vapor delivery ports configured to deliver a flow of vapor from the needle into prostate tissue. The vapor delivery device 900 can be connected to a light source 940, a vapor source 250, a controller 255, an aspiration source 320, and a fluid source 914. In one method, the trans-urethral vapor delivery device of FIG. 9 can be inserted into a urethra of a patient, a needle of the vapor delivery device can be extended into the prostate, and vapor can be delivered from the device into the prostate to treat prostate cancer. In one specific embodiment, the needle of the vapor delivery device can be extended from the urethra, through the transition zone, and into the peripheral zone. Vapor can be delivered from the device into the peripheral zone tissue to treat prostate cancer.

Figure 10:
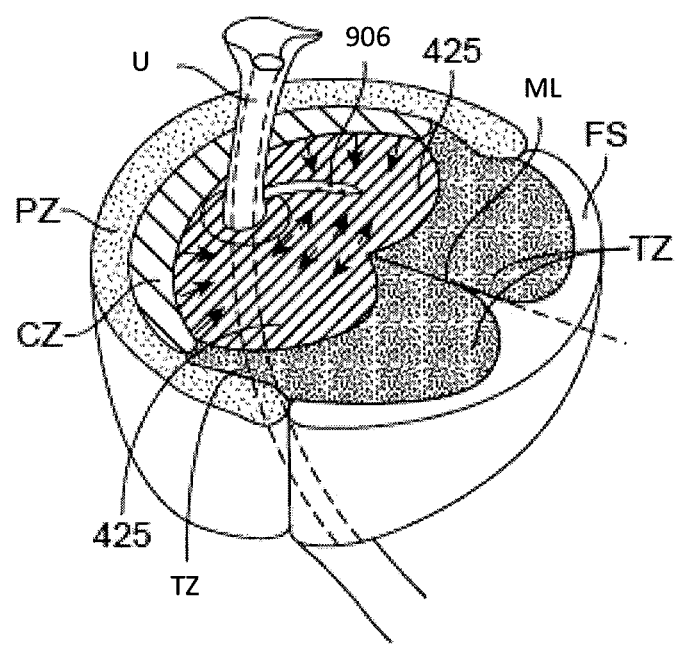
FIG. 10 is a sectional view of a prostate being treated with vapor therapy trans-urethrally.

FIG. 10 is a cutaway view of the device 900 of FIG. 9 with the vapor delivery needle 906 extended into the prostate from the urethra U. As shown, the needle is inserted into one of the two lobes of the prostate, which are separated by imaginary mid-line ML. Although the needle is shown inserted into the transition zone TZ of the prostate, it should be understood that the needle can also be extended into the other regions of the prostate, including the peripheral zone or the central zone. Upon delivering vapor from the needle into the prostate, the ablation zone 425 can be seen in the Figure. The size and depth of the ablation zone can be controlled depending on the duration of vapor delivery and the amount and quality of vapor delivered.

Figure 11:
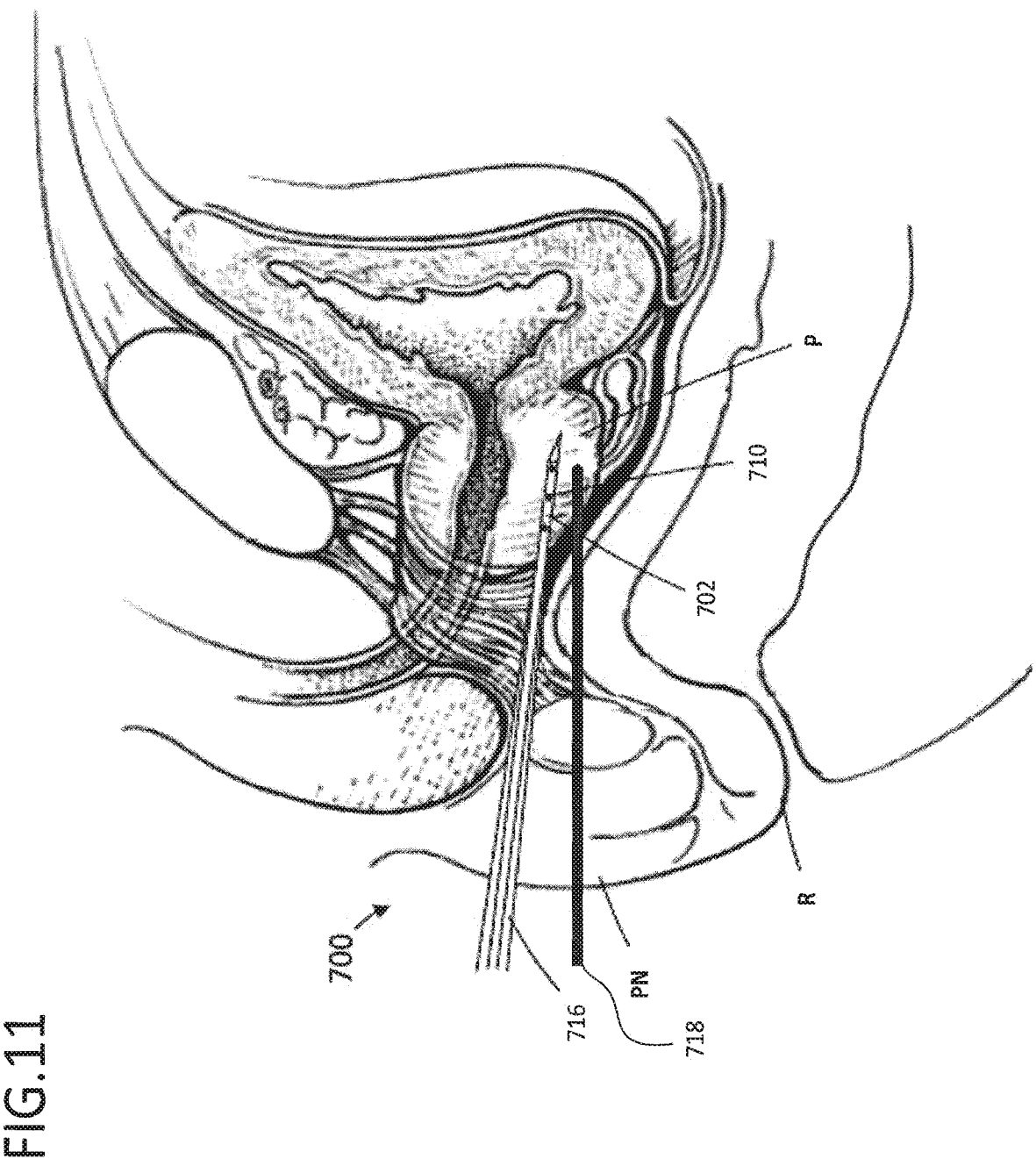
FIG. 11 shows one embodiment of measuring a temperature of a prostate while delivering vapor therapy to the prostate.

FIG. 11 shows a method similar to that shown in FIG. 7 above. However, in FIG. 11, a temperature probe 718 is also inserted through the perineal tissue and advanced towards the prostate. Instead of piercing the prostate with the temperature probe, as is done with the vapor delivery needle, the temperature probe can be placed on an outside surface of the prostate, such as along the outside of the peripheral zone of the prostate, or can be placed in tissues surrounding the prostate. In one embodiment, saline can be injected into the tissues in which the temperature probe is placed (either before or after insertion of the temperature probe) to act as a heat sink. Vapor can be delivered into the prostate with vapor delivery needle 702, as described above, and the temperature can be monitored with the temperature probe 718. Vapor delivery can then be terminated when the monitored temperature reaches a desired level. In one embodiment, vapor can be delivered into the prostate with the vapor delivery needle until an exterior portion of the prostate reaches a temperature of 47-52 degrees C. Temperature probe 718 can comprise a singular or linear array of temperature sensors such as thermocouples, with vapor therapy terminated when any sensor in the array exceeds a predefined limit. Temperature probe 718 can comprise an array of ultrasound transducers which produce a three dimensional ultrasound image of surrounding tissue. The ultrasound array image may provide a temperature map of tissue in addition to guiding needle placement within tissue.

Figure 12:
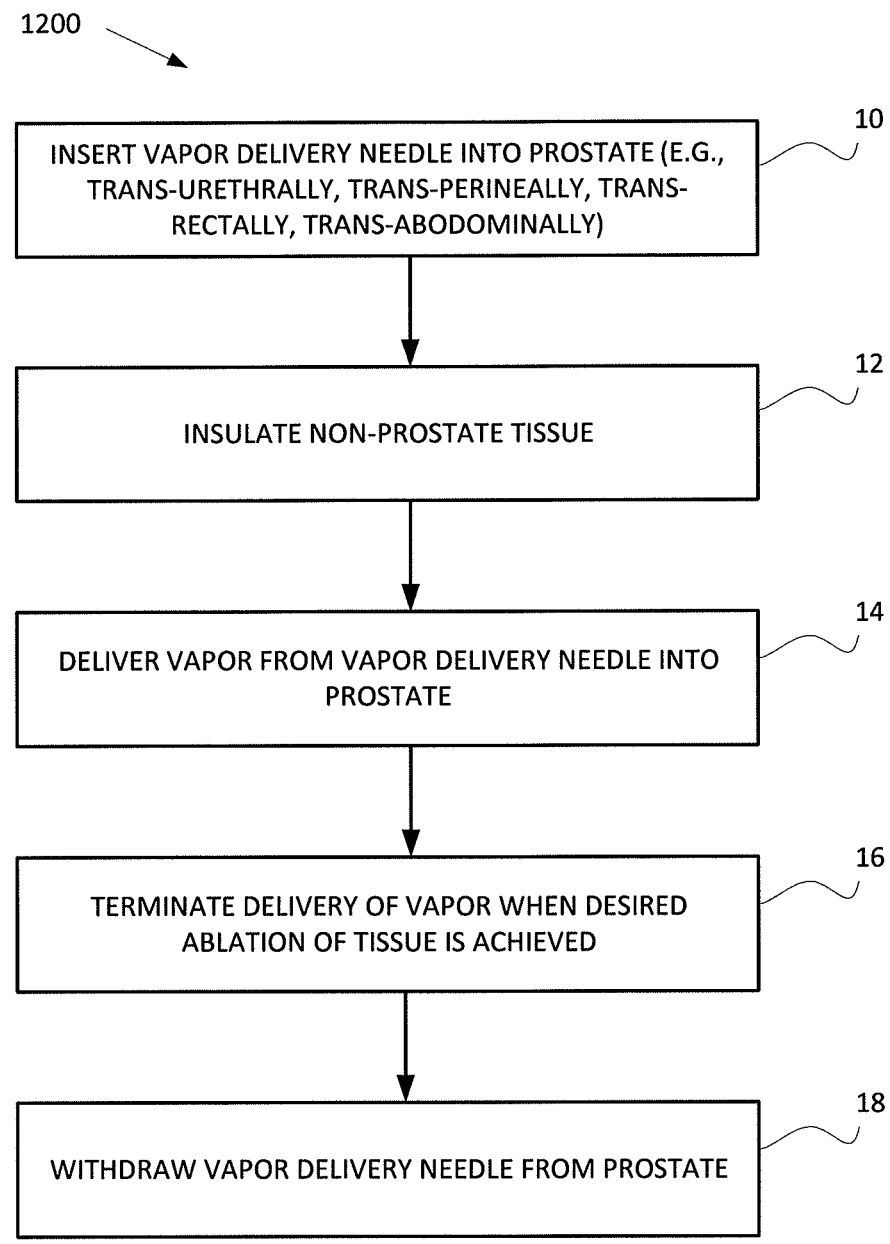
FIG. 12 is a flowchart illustrating one method of treating prostate tissue.
Figure 13:
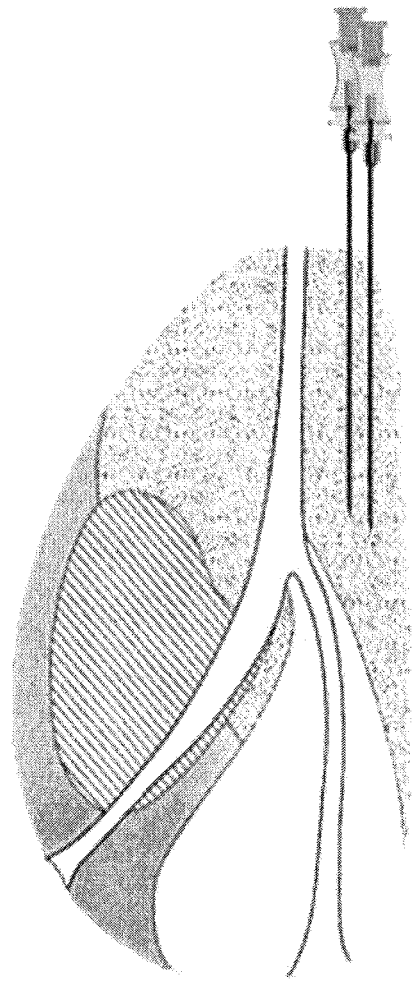
FIG. 13 is a figure showing two vapor delivery needles inserted into the prostate simultaneously.

FIG. 12 illustrates a flow chart 1200 to describe the various methods described above. At step 10 of flowchart 1200, a vapor delivery needle can be inserted into the prostate of a patient. The needle can be inserted into the prostate trans-perineally (FIGS. 7 and 11), trans-urethrally (FIG. 10), trans-rectally, or trans-abdominally. Any of the vapor delivery devices described herein can be used for this method step. In some embodiments, the vapor delivery needle can be inserted into a peripheral zone of the prostate. In other embodiments, the needle can be inserted into a transition zone, or alternatively, into a central zone of the prostate.

Next, at step 12 of flowchart 1200, the method can optionally include insulating non-prostate tissues from the vapor delivery needle with an insulating layer or sheath around a portion of the vapor delivery needle. Embodiments of an insulating layer or sheath are found in FIGS. 6A-6B above.

Next, at steps 14 and 16 of flowchart 1200, vapor can be delivered from the vapor delivery needle into the prostate, and delivery of vapor can be terminated when the desired ablation of prostate tissue is achieved. In some embodiments, vapor can be delivered for a period of between 1-60 seconds to ablate the prostate tissue. Alternatively, in another embodiment the vapor can be delivered for a period of between 9-12 seconds. In some embodiments, ablating the prostate tissue comprises ablating prostate cancer tissue. In one embodiment, ablating prostate tissue can comprise ablating peripheral zone tissue without ablating non-peripheral zone tissue. In one embodiment, the temperature of the prostate, or the temperature of tissue just outside the prostate (e.g., the connective or fatty tissues, or the nerves surrounding the prostate, or the prostate capsule) can be monitored (as described in FIG. 11) and therapy can be terminated when the prostate reaches a desired temperature (e.g., 44-60 degrees C.). In one embodiment, the desired temperature of monitored outer boundary of the ablation is approximately 48 degrees C.

Finally, at step 18 of flowchart 1200, the vapor delivery needle can be withdrawn from the prostate after the therapy is completed. In some embodiments, the needle can remain hot while being withdrawn so as to seal the prostate and intervening tissues as the needle is withdrawn. In another embodiment, the needle can continue to release a flow of vapor as the needle is withdrawn, to seal the prostate and intervening tissues. The "hot" needle, or continuing to release vapor as the needle is withdrawn can kill cancer cells and prevent "seeding" or spreading of cancer cells into non-cancerous tissue as the needle is withdrawn.

This disclosure describes a vapor delivery system for ablating tissues of the prostate that has a number of unique advantages over other energy modalities.

First, systems described herein benefit from a reduced procedure time. In some embodiments, vapor therapy of the prostate comprises one or more short (<12 sec) treatments of vapor delivery. Other energy modalities, such as RF, microwave, ultrasound, laser, radiation seeds, or surgical resection require much longer treatment times. The shorter procedure times provided by vapor therapy allow for less chance of collateral damage, and less time for heat conduction to, and thermal damage of, adjacent tissues. Vapor therapy also provides for reduced energy application, which enables the shorter treatment time described above. Vapor therapy provides very little excess energy that can cause collateral damage.

Furthermore, vapor therapy provides thermal ablation of tissue with a limited maximum temperature. Vapor temperature is nominally ~100° C. Interstitial tissue pressure may be around 1 psi (50 mm Hg), and vapor at 1 psi (gauge pressure) has a temperature less than 102° C. Vapor will condense only on tissues having temperature lower than steam temperature. Therefore, in vapor therapy, tissue temperature is equal to or less than the temperature of the vapor. The result of vapor therapy in tissue is that tissue remains moist with no charring or scaring, such as is found in RF or other ablative technologies. Furthermore, tissue treated with vapor therapy can be completely absorbed by the body over time. The other thermal therapies mentioned (e.g., RF, ultrasound, laser, etc.) have no tissue temperature limit, so tissue treated with these modalities can be desiccated, charred, or encapsulated with scar formation. Heat can also be conducted with these modalities to adjacent tissue at higher temperatures, causing increased collateral damage.

Vapor therapy is contained within the prostate capsule or desired prostate zone capsule. Vapor does not pass through the capsule tissue that surrounds the lobe or each prostate zone being treated. Additionally, tissue constricts around a vapor delivery needle, preventing vapor escape. The capsule tissue has reduced thermal conductivity, thereby insulating surrounding tissue from treated prostate tissue. Untreated tissue surrounding the prostate capsule is perfused with blood. Perfusion efficiently removes heat, keeping the outside surface of the capsule at a significantly lower temperature than treated tissue within the capsule, preventing necrosis on or outside the capsule, and preventing nerve damage.

The prostate capsules are not a barrier to other ablation therapies. The electrical properties of the capsule and surrounding tissue are similar to those of the prostate, allowing ablation current to cross the prostate capsule in RF, microwave and other electromagnetic or radiation therapies. The capsule does not contain ultrasound vibrational energy, and does not confine cryotherapy. Mechanical therapies can readily cross the boundaries of the capsule.

Furthermore, vapor can fill a treatment volume, even when delivered from a small source, such as a vapor delivery needle. Vapor can penetrate through the spaces around cells in the prostate. Thermal diffusion through the tiny cell volume occurs in a few milliseconds, so tissue through which steam has passed can be rapidly elevated to ablation temperature. Vapor will not condense on tissue already at 100° C. Intercellular spaces constrict when vapor condenses. Vapor will therefore take the path of least resistance and lower temperature through intercellular spaces that do not already contain condensed steam. Lesions are therefore spherical in vapor therapy. Vapor will continue to condense on any tissue that is below steam temperature as it moves radially outward into tissue.

At the end of vapor therapy, heat can be conducted to surrounding tissue. If this tissue is perfused, conducted heat may be carried away, keeping the tissue surrounding the ablation zone below ablation temperature. The volume of a lesion from vapor therapy can be therefore predicted by the energy content of the vapor (mass of fluid delivered as vapor times its heat of vaporization) which is equal to the volume of the lesion times the prostate tissue specific heat (Joules/$cm^{3}$° C.) times the difference between vapor temperature 100° C.) and body temperature ($\approx$37° C.). For vapor delivered at a constant rate, the volume of the lesion is simply proportional to the delivery time.

Although particular embodiments of the present invention have been described above in detail, it will be understood that this description is merely for purposes of illustration and the above description of the invention is not exhaustive. Specific features of the invention are shown in some drawings and not in others, and this is for convenience only and any feature may be combined with another in accordance with the invention. A number of variations and alternatives will be apparent to one having ordinary skills in the art. Such alternatives and variations are intended to be included within the scope of the claims. Particular features that are presented in dependent claims can be combined and fall within the scope of the invention. The invention also encompasses embodiments as if dependent claims were alternatively written in a multiple dependent claim format with reference to other independent claims.

What is claimed is:

1. A method for treating prostate cancer, comprising:
delivering vapor into a peripheral zone lobe in a prostate so as to provide between 300 and 1000 calories of energy to the peripheral zone lobe and thereby ablate all of the tissue in the peripheral zone lobe, wherein the delivering the vapor includes delivering a first flow of vapor via a needle, and wherein the method further comprises delivering a second flow of vapor while withdrawing the needle from the prostate.

2. A method for treating prostate cancer, comprising:
positioning a needle into a peripheral zone lobe in a prostate;
delivering a first flow of vapor from the needle into the peripheral zone lobe so as to provide less than 150 calories of energy to the peripheral zone lobe and thereby ablate malignant tissue in the peripheral zone lobe; and
delivering a second flow of the vapor from the needle while withdrawing the needle from the prostate.

3. The method of claim 2 wherein a volume of the delivered first flow of the vapor is adapted for said ablation of malignant tissue in the peripheral zone lobe.

4. The method of claim 2 further comprising re-positioning the needle in the peripheral zone lobe and repeating the delivering step at a second site to further ablate malignant tissue in the peripheral zone lobe.

5. The method of claim 2 further comprising:
measuring a temperature of the prostate; and
terminating delivery of the first flow of the vapor when the temperature of the prostate reaches a pre-determined threshold.

6. The method of claim 5 wherein the measuring step comprises measuring a temperature of an outer capsule of the prostate.

7. The method of claim 5 wherein the pre-determined threshold is between 44 and 60 degrees C.

8. The method of claim 2 wherein the delivering the second flow of the vapor seals a prostate capsule.

9. The method of claim 2 wherein the delivering the second flow of the vapor inhibits spreading of cancer cells into non-cancerous tissue.

* * * * *